US008142394B1

(12) United States Patent
Rotella et al.

(10) Patent No.: US 8,142,394 B1
(45) Date of Patent: Mar. 27, 2012

(54) ENTERAL FEEDING CATHETER DEVICE WITH AN INDICATOR

(75) Inventors: John A. Rotella, Roswell, GA (US); Adrienne A. Hershey, Cumming, GA (US); Donald J. McMichael, Roswell, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 12/977,359

(22) Filed: Dec. 23, 2010

(51) Int. Cl.
 *A61M 29/00* (2006.01)
(52) U.S. Cl. ................................. 604/100.03
(58) Field of Classification Search ............... 604/97.03, 604/100.01, 100.02, 100.03
See application file for complete search history.

(56) References Cited

U.S. PATENT DOCUMENTS

| | | | |
|---|---|---|---|
| 3,630,198 A * | 12/1971 | Henkin | 604/170.01 |
| 3,642,005 A | 2/1972 | McGinnis | |
| 3,780,693 A | 12/1973 | Parr | |
| 4,245,639 A * | 1/1981 | La Rosa | 604/97.02 |
| 4,266,550 A | 5/1981 | Bruner | |
| 4,384,584 A * | 5/1983 | Chen | 604/28 |
| 4,502,490 A | 3/1985 | Evans et al. | |
| 4,522,194 A | 6/1985 | Normann | |
| 5,103,817 A | 4/1992 | Reisdorf et al. | |
| 5,201,755 A | 4/1993 | Klement | |
| 5,218,970 A | 6/1993 | Turnbull et al. | |
| 5,496,311 A | 3/1996 | Abele et al. | |
| 5,792,070 A | 8/1998 | Kauphusman et al. | |
| 6,004,305 A * | 12/1999 | Hursman et al. | 604/328 |
| 6,082,361 A * | 7/2000 | Morejon | 128/207.15 |
| 6,536,260 B2 | 3/2003 | Williams | |
| 6,732,734 B2 | 5/2004 | Ogushi et al. | |
| 6,878,130 B2 | 4/2005 | Fournie et al. | |
| 6,916,307 B2 | 7/2005 | Willis et al. | |
| 7,018,359 B2 | 3/2006 | Igarashi et al. | |
| 7,195,612 B2 | 3/2007 | van Sloten et al. | |
| 7,383,736 B2 | 6/2008 | Esnouf | |

(Continued)

FOREIGN PATENT DOCUMENTS

WO WO 03/101372 A1 12/2003

OTHER PUBLICATIONS

Co-Pending U.S. Appl. No. 12/645,553, filed Dec. 23, 2009.

*Primary Examiner* — Nicholas Lucchesi
*Assistant Examiner* — Aarti B Berdichevsky
(74) *Attorney, Agent, or Firm* — Dority & Manning, P.A.

(57) ABSTRACT

A balloon catheter device, for example an enteral feeding catheter, includes a catheter having a proximal end, a distal end, and catheter walls defining a catheter lumen. A base is located at the proximal end of the catheter and has an opening to the catheter lumen. An inflatable balloon is located at a distal end of the catheter and is inflated through an inflation valve located on the base. An internal cavity is defined in the base and is in fluid communication with the inflatable balloon such that fluid used to inflate the balloon to an operational fill volume fills the internal cavity as well. A translucent window is disposed over the internal cavity such that an interior volume of the cavity is externally viewable. Introduction of a colored fluid through the inflation valve to inflate the balloon results in the colored fluid also being present in the internal cavity, thereby providing an externally visual indication of the inflation state of the balloon.

10 Claims, 5 Drawing Sheets

U.S. PATENT DOCUMENTS

| | | | |
|---|---|---|---|
| 7,404,329 B2 | 7/2008 | Quinn et al. | |
| 2002/0045854 A1* | 4/2002 | Royo et al. | 604/97.03 |
| 2002/0115962 A1* | 8/2002 | Fawcett | 604/97.02 |
| 2004/0097813 A1 | 5/2004 | Williams | |
| 2004/0106899 A1 | 6/2004 | McMichael et al. | |
| 2004/0106901 A1* | 6/2004 | Letson et al. | 604/104 |
| 2004/0267195 A1 | 12/2004 | Currlin | |
| 2005/0197667 A1* | 9/2005 | Chan et al. | 606/194 |
| 2006/0271088 A1* | 11/2006 | Alfrhan | 606/192 |
| 2007/0010787 A1* | 1/2007 | Hackett et al. | 604/96.01 |
| 2007/0208301 A1* | 9/2007 | Evard et al. | 604/103.1 |
| 2008/0146993 A1 | 6/2008 | Krishna | |
| 2008/0208240 A1 | 8/2008 | Paz | |
| 2008/0228138 A1 | 9/2008 | van Sloten et al. | |
| 2009/0312701 A1* | 12/2009 | Gobel et al. | 604/96.01 |
| 2010/0185155 A1* | 7/2010 | McMichael et al. | 604/175 |
| 2010/0185159 A1* | 7/2010 | Bagwell et al. | 604/256 |
| 2010/0217185 A1 | 8/2010 | Terliuc et al. | |
| 2010/0228192 A1 | 9/2010 | O'Dea et al. | |
| 2010/0312181 A1 | 12/2010 | O'Dea | |
| 2011/0082444 A1* | 4/2011 | Mayback et al. | 604/544 |
| 2011/0152762 A1* | 6/2011 | Hershey et al. | 604/99.02 |

* cited by examiner

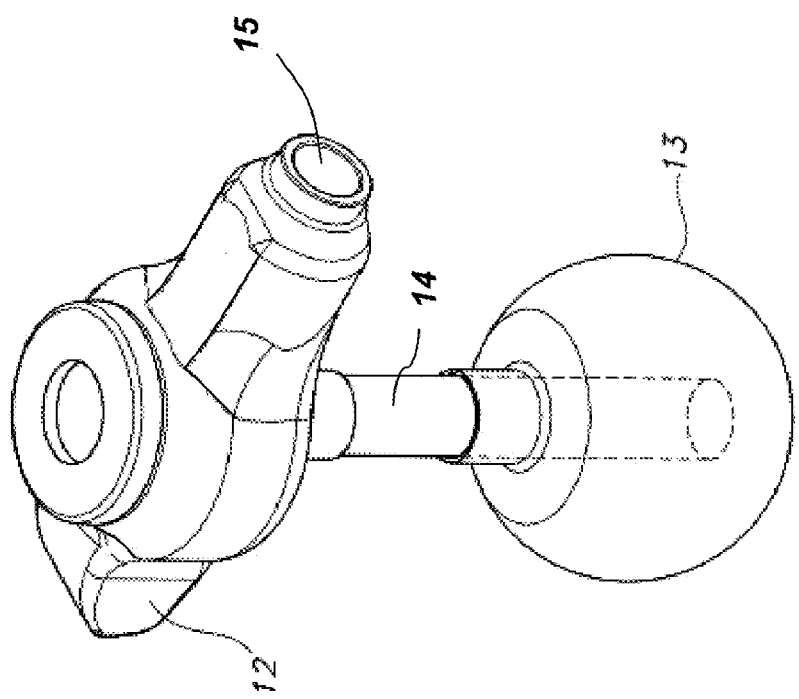
Fig. -1B-
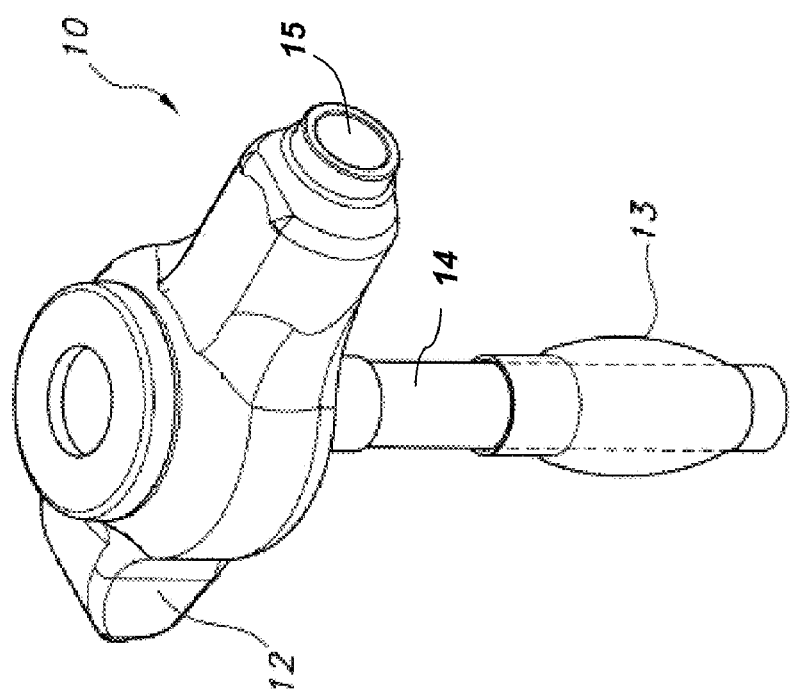
Fig. -1A-

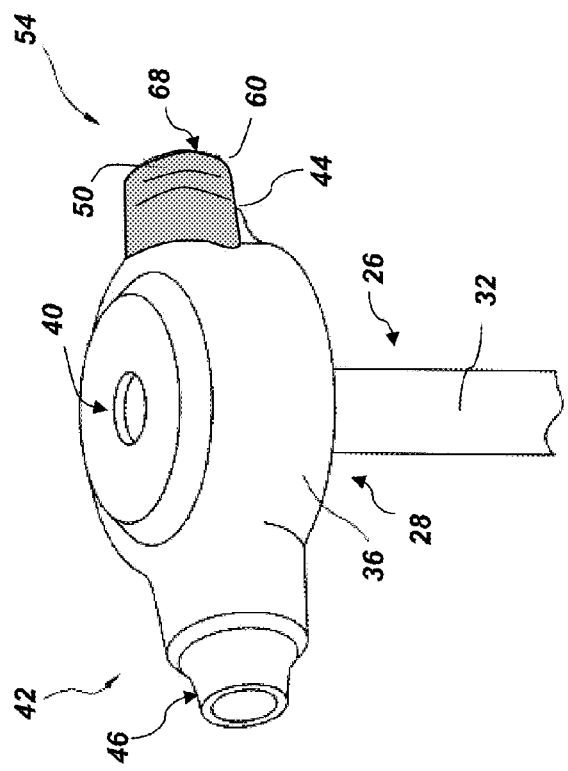
*Fig. -2B-*
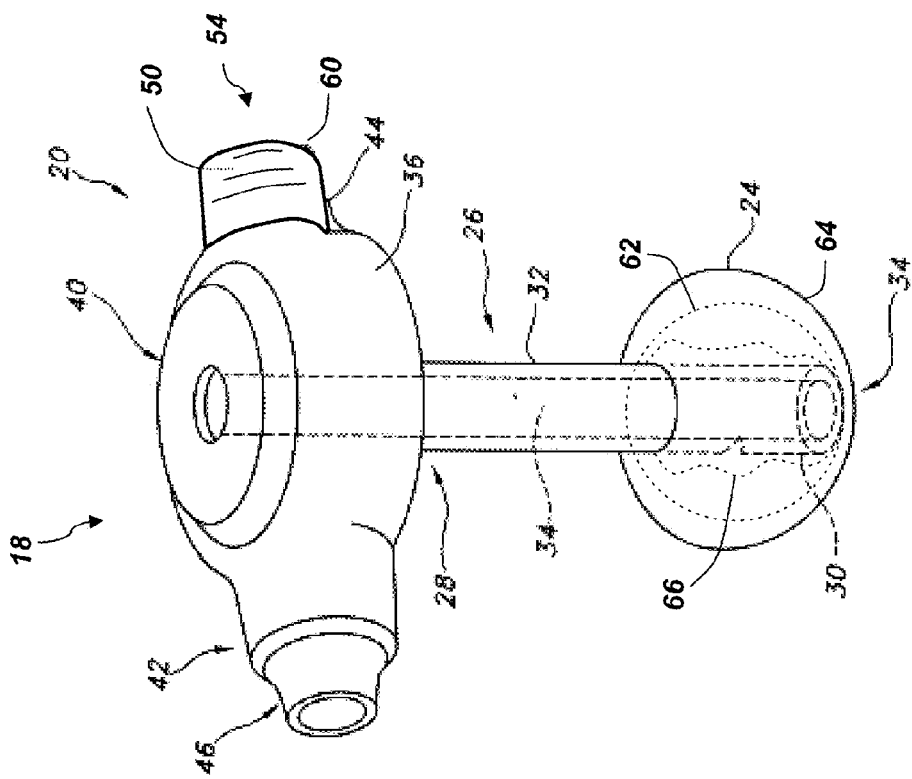
*Fig. -2A-*

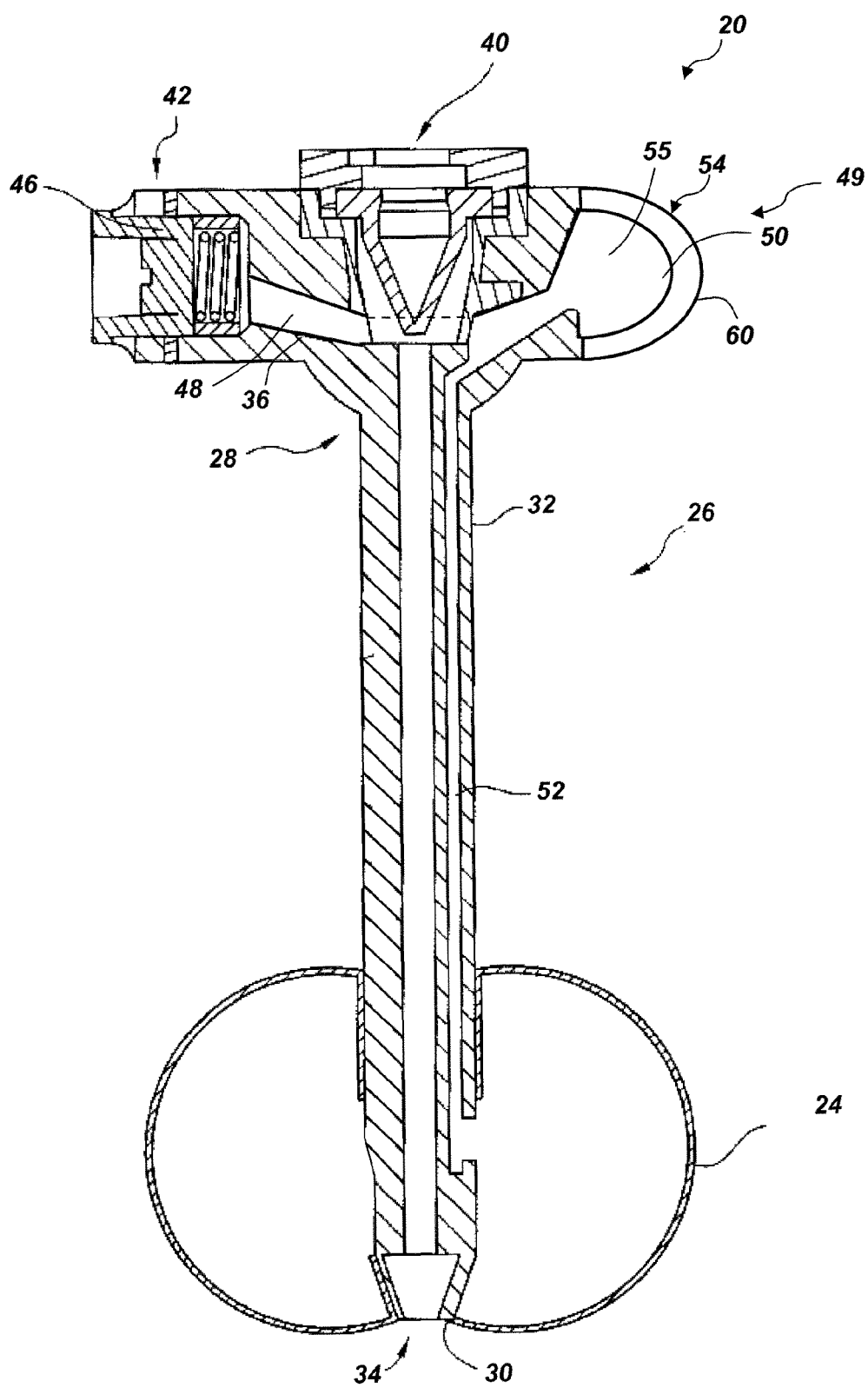
Fig. -3-

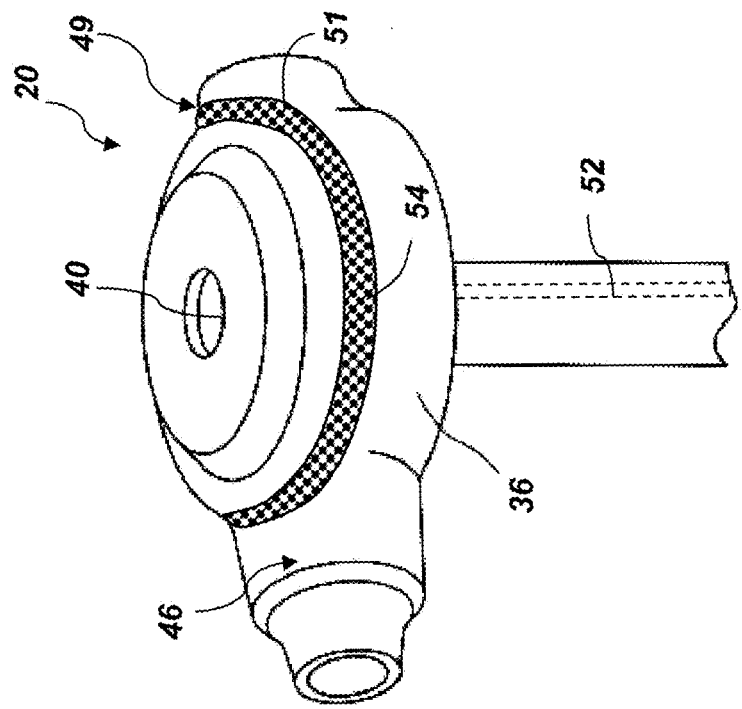
*Fig. -4B-*
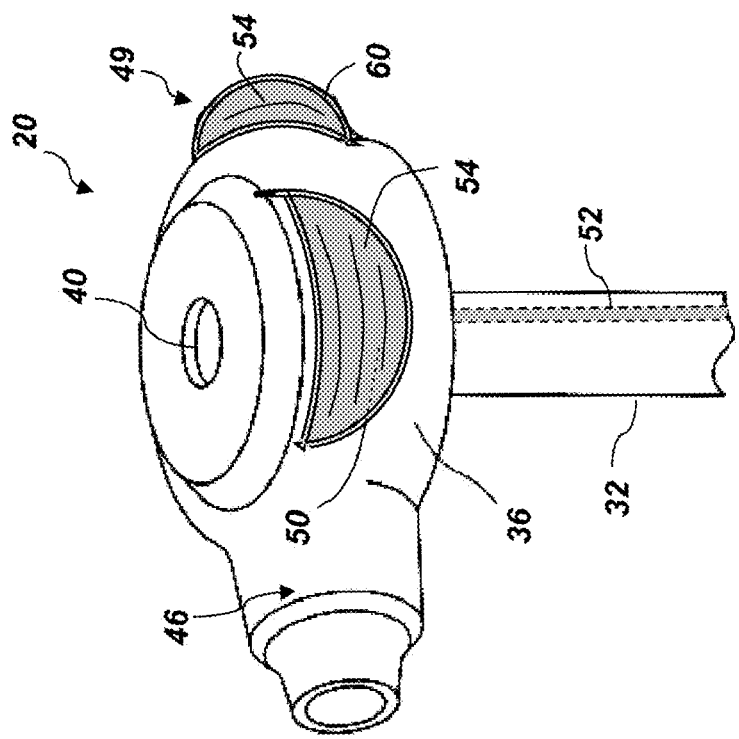
*Fig. -4A-*

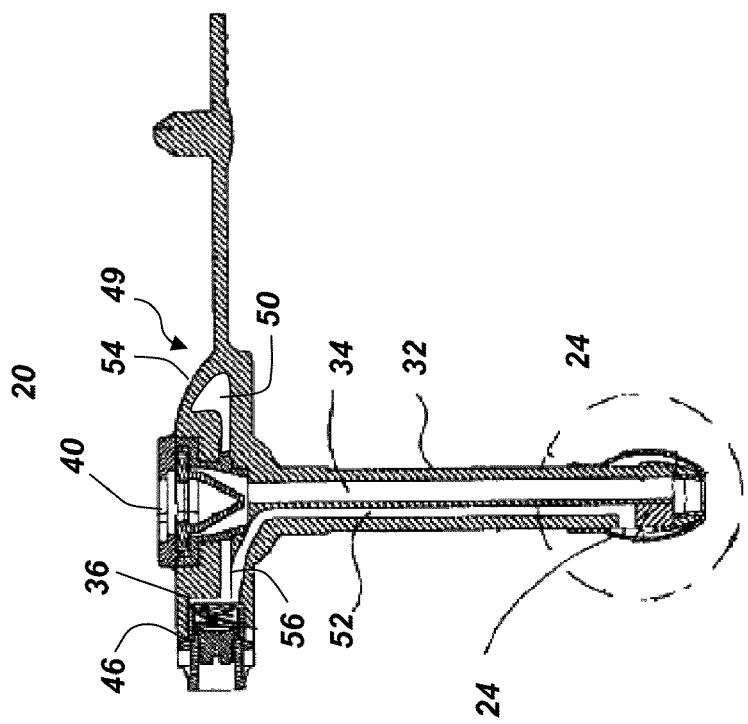
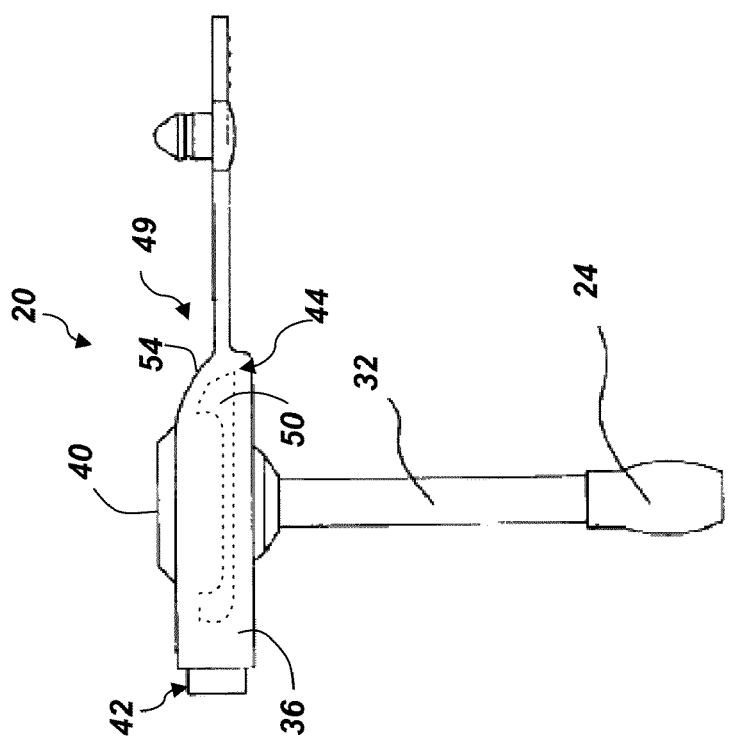
Fig. -5B-
Fig. -5A-

ENTERAL FEEDING CATHETER DEVICE WITH AN INDICATOR

FIELD OF THE INVENTION

The present invention relates generally to balloon catheters, and more particularly to improved gastrostomy tubes or enteral feeding catheters.

BACKGROUND

Numerous situations exist in which a body cavity needs to be catheterized to achieve a desired medical goal. One relatively common situation is to provide nutritional solutions or medicines directly into the stomach or intestines. A stoma is formed in the stomach or intestinal wall and a catheter is placed through the stoma. This surgical opening and/or the procedure to create the opening is common referred to as "gastrostomy". Feeding solutions can be injected through the catheter to provide nutrients directly to the stomach or intestines (known as enteral feeding). A variety of different catheters intended for enteral feeding have been developed over the years, including some having a "low profile" relative to the portion of the catheter which sits on a patient's skin, as well as those having the more traditional or non-low profile configuration. These percutaneous transport catheters or tubes are frequently referred to as "gastrostomy tubes", "percutaneous gastrostomy catheters", "PEG tubes" or "enteral feeding catheters".

To prevent the PEG tube from being pulled out of the stomach/intestinal wall, various types of retainers are used at a distal end of the catheter. Examples of conventional devices with Malecot tips or similar expanding tips are found at, for example, U.S. Pat. No. 3,915,171 for "Gastrostomy Tube" issued to Shermeta; U.S. Pat. No. 4,315,513 for "Gastrostomy and Other Percutaneous Transport Tubes" issued to Nawash et al.; U.S. Pat. No. 4,944,732 for "Gastrostomy Port" issued to Russo; and U.S. Pat. No. 5,484,420 for "Retention Bolsters for Percutaneous Catheters" issued to Russo. Exemplary commercial products include the Passport® Low Profile Gastrostomy Device available from Cook Medical, Inc. of Bloomington, Ind. and the Mini One™ Non-Balloon Button available from Applied Medical Technology, Inc. of Brecksville, Ohio. A shortcoming of these devices relates to the manner of insertion and withdrawal of a catheter or tube incorporating these retaining fixtures (e.g., a gastrostomy tube) into a body lumen such as into the stomach.

Balloons can be used in place of these conventional devices with Malecot tips or similar expanding tips. A balloon, typically made of a "soft" or elastomeric medical grade silicone, is attached to the end of the catheter and is deflated for insertion through the stoma and then inflated to hold the enteral feeding assembly in position. While these balloons have many advantages, balloons may eventually leak and deflate. In addition, "soft" or elastomeric medical grade silicone has a tendency to "creep" or stress relax over time which can change the dimensions of the balloon.

Various types of medical devices incorporating inflatable balloons devices are known and widely used in the medical field. For example, endotracheal tubes and tracheostomy tubes utilize inflatable balloons to create a seal that prevents the passage of mucus into the lungs. Pilot balloons, pressure gauges, and inflation indicators are used to provide a continuous reading of the pressure in the balloon in these devices. That is, these devices provide an output that conveys continuous or uninterrupted information showing pressure increases and decreases in the balloon. These devices are described at, for example, U.S. Pat. No. 3,642,005 for "Endotracheal Tube With Inflatable Cuff" issued to McGinnis; U.S. Pat. No. 4,266,550 for "Pressure Indicators For Inflatable Cuff-Type Catheters" issued to Bruner; U.S. Pat. No. 6,732,734 for "Pilot Balloon For Balloon Catheters" issued to Ogushi et al.; and U.S. Pat. No. 7,404,329 for "Pressure Gauge For Use With An Airway Lumen" issued to Quinn et al.

In addition to pilot balloons, pressure indicators incorporating bellows or diaphragms are known and electronic pressure indicators are known. For example, a simple bellows pressure indicator for showing continuous reading of fluid pressure is described in U.S. Pat. No. 3,780,693 for "Visible Fluid Pressure Indicator" to Parr. U.S. Pat. No. 7,383,736 "Device and Method for Pressure Indication" issued to Esnouf, describes a bellows device for use with a laryngeal mask balloon or other airway management equipment incorporating balloons. The device of Esnouf incorporates a bellows that is displaced by a differential pressure between the outside of the bellows and the inside of the bellows to provide a continuous reading of the increases and decreases in the pressure of fluid in the balloon. U.S. Pat. No. 7,018,359 for "Inner Pressure Indicator of Cuff" issued to Igarashi et al., describes a bellows or spring structure for use with a tracheostomy tube balloon or endotracheal tube. The device of Igarashi et al. is connected to the balloon through an inflation tube and has an inflation valve at the other end that is connected to a syringe. The device uses a bellows and/or spring indicator provide a continuous reading and display of the increase and decrease in the pressure of fluid in the balloon through movement of the bellows against a numerical scale printed on the housing. U.S. Pat. No. 5,218,970 for "Tracheal Tube Cuff Pressure Monitor" issued to Turnbull et al. describes a continuous pressure monitor for a tracheal tube incorporating an electronic pressure sensor such as a silicon strain gauge pressure sensor, a processor that performs various calibration, scaling and calculation operations on the signal from the sensor and provides an output to a numeric display conveying a continuous reading of the increases and decreases in the pressure of fluid in the balloon.

These indicators are adapted for airway devices where careful and constant monitoring of balloon pressure is important. In order to adequately seal the space between the lumen of the trachea and the balloon, there is a tendency to overinflate the balloon, which may result in tissue damage. If the pressure is too low, the balloon does not adequately seal the space between the lumen of the trachea and the balloon thereby allowing secretions to enter the lungs causing pneumonia and other respiratory complications. In order to provide careful control of the balloon pressure, these pilot balloons, bellows and diaphragm indicators and electronic sensors are designed to convey a continuous reading of the increases and decreases in the pressure of fluid in the balloon.

While this level of sensitivity and continuous reading is desirable, pilot balloons and similar bellows or diaphragm indicators are relatively large and typically require skill and experience to accurately interpret the output of these conventional devices as they provide a continuous reading of pressure. While electronic pressure sensors are accurate and are generally easy to read, they are relatively large and expensive. Scaling these types of devices down to a sufficiently small size so they can be used with a low-profile PEG tube only highlights the problems associated with the size, calibration, accuracy, and reading or interpreting the output of these devices.

U.S. Pat. No. 6,878,130 for "External Inflation Indicator for a Low Profile Gastrostomy Tube" issued to Fournie et al. describes an external inflationary indicator similar to a pilot balloon integrated into the base of a gastrostomy device having a retainer balloon. The device of Fournie et al. provides a continuous tactile reading of the inflationary state of the retainer balloon. The Fournie et al. device utilizes two generally bubble-like portions that assume a generally convex shape when the retainer balloon is inflated and a generally concave shape when the balloon is deflated. The changing shape of these generally bubble-like portions provides a continuous tactile indication or reading of the inflationary state of the balloon. In addition, the external inflationary indicator provides continuous visual indication of the inflationary state of the retainer balloon through the use of a separating bar dividing these two generally bubble-like portions of the indicator.

The separating bar visually separates as the balloon becomes fully inflated to indicate the inflationary state.

The device of Fournie et al. is relatively complicated and adds significantly to the manufacturing process and costs. In addition, the indicator increases the overall profile (i.e., shape, height, etc.) of the head, which is generally undesirable to the user. In addition, the use of moving, mechanical indicator components is always prone to failure or malfunction of such components, which results in a complex medical procedure to replace the device.

Accordingly, there is a need for a relatively simple yet reliable pressure change indicator that can be readily integrated into the head of a PEG tube without unduly increasing the size or mechanical complexity of the head, and which is easy to view externally.

SUMMARY OF THE INVENTION

Objects and advantages of the invention will be set forth in part in the following description, or may be obvious from the description, or may be learned through practice of the invention.

The present invention provides a balloon catheter device incorporating an indicator that provides a discrete visual signal about the inflation condition of a balloon associated with the catheter. For example, the indicator provides a discrete visual signal that the volume of the balloon is different from an operational volume due to a partial or full loss of fluid used to inflate the balloon. In a particular embodiment, the indicator is disposed wholly within the base and is externally visible through the base. In another embodiment, the indicator may include a cap that is attached to an end or other circumferential position on the base.

According to an aspect of the invention, the balloon catheter device may be an enteral feeding catheter that includes a catheter having a proximal end, a distal end, and catheter walls defining a catheter lumen. A base is located at the proximal end of the catheter. An opening to the catheter lumen is defined in the base. The base may be variously configured with any desired shape or profile, and in one embodiment has a first end and a second end. An inflatable balloon is located at a distal end of the catheter. In one embodiment, the balloon may be an elastomeric balloon that stretches and expands generally continuously with increasing inflation pressure from an initial un-inflated state to an operational fill volume. In an alternate embodiment, the balloon may be configured with a collapsed, non-distended state and expands with negligible inflation pressure to an initial distended state in which the material that forms the balloon is smooth and completely unfolded but prior to any meaningful stretching of the material. The balloon is then further pressurized with fluid to an operational fill volume that is generally no more than about 1.5 times (i.e., about 50 percent greater than) the volume of the balloon at its initial distended state.

The catheter device includes an inflation valve located in the base. The inflation valve is in fluid communication with the balloon through, for example, an inflation lumen defined by a portion of the wall of the catheter. An external inflation lumen or other configurations are also contemplated. The inflation valve may desirably be located on the first end of the base.

The indicator is configured as an internal cavity defined partially or wholly in the base that is in fluid communication with the inflatable balloon such that fluid used to inflate the balloon to its operational fill volume also fills the internal cavity. A translucent window is disposed over the internal cavity such that the interior volume of the cavity is externally viewable through the translucent window. With this configuration, introduction of a colored (i.e., non-clear) fluid through the inflation valve to inflate the balloon results in the colored fluid flowing into the internal cavity and being externally distinguishable through the translucent window, thereby providing an externally visual indication of the inflation state of the balloon. For example, the internal cavity may be configured to provide a discrete visual signal through the translucent window that the balloon is no longer inflated or is no longer at its operational fill volume.

In a particular embodiment, the inflation valve is location on the first end of the base and the internal cavity and translucent window are located on the second end of the base.

The internal cavity may be disposed is in fluid communication with the balloon in various ways. For example, an indicator lumen may be defined longitudinally along the catheter between the balloon and the internal cavity. In another embodiment, a flow passage may be defined between the inflation lumen and the internal cavity.

In certain embodiments, the internal cavity and associated translucent window are defined at a single discrete location on the base, for example at a second end of the base opposite from the inflation valve. In other embodiments, the internal cavity and associated translucent window may be defined at a plurality of discrete locations on the base, or completely around the base.

The translucent window may be an insert of translucent material disposed within an opaque portion of the base in which the internal cavity is formed. In an alternate embodiment, the portion of the base in which the internal cavity is formed may be inherently translucent such that the translucent window is defined by the portion of the base overlying the internal cavity.

The present invention also may include a source of fluid to inflate the balloon, with the fluid having a color that is visually distinguishable from the base through the translucent window.

Any manner of additional or supplemental indicators may be provided within the internal cavity. For example, a brightly colored plate or insert (or a member with a visually distinguishable pattern or texture) may be disposed within the internal cavity so as to be visible through the translucent window. Introduction of colored inflation fluid in the cavity may obscure or hide such member, thereby giving an additional visual indication that the balloon is inflated. In other words, if the distinguishing member is not visible, then the balloon is inflated.

In other aspects, the present invention includes method embodiments for providing an externally viewable visual indication of failure or malfunction of a balloon component of a balloon catheter, such as an enteral feeding catheter. The method includes inflating the balloon with a fluid that has a visually distinguishable non-clear color, the balloon being in fluid communication with a translucent portion of a base component of the catheter. In this manner, the presence of the colored fluid in the base is visually distinguishable through the base component and provides a visual indication that the balloon is at a predetermined inflated state. Visual absence of all or a portion of the colored fluid in the base is a visual indication that the balloon is no longer inflated to its operational fill volume.

BRIEF DESCRIPTION OF THE DRAWINGS

FIG. 1A is a perspective view of an exemplary prior art device;

FIG. 1B is a perspective view of the device of FIG. 1 with the balloon in an expanded state;

FIG. 2A is a perspective and view of an exemplary enteral feeding catheter assembly incorporating an internal indicator in accordance with aspects of the invention;

FIG. 2B is a perspective view of the base of the device of FIG. 2A with a change of state of the indicator;

FIG. 3 is a cross-sectional side view of an exemplary enteral feeding catheter assembly incorporating an indicator.

FIG. 4A is a perspective view of the base portion of an additional exemplary enteral feeding catheter assembly incorporating an indicator;

FIG. 4B is a perspective view of the device of FIG. 4A with a change of state of the indicator;

FIG. 5A is a side view of an alternative exemplary enteral feeding catheter assembly incorporating an indicator; and FIG. 5B is a side cross-sectional view of the device of FIG. 5A;

DETAILED DESCRIPTION OF THE INVENTION

Reference will now be made in detail to one or more embodiments of the invention, examples of the invention, examples of which are illustrated in the drawings. Each example and embodiment is provided by way of explanation of the invention, and is not meant as a limitation of the invention. For example, features illustrated or described as part of one embodiment may be used with another embodiment to yield still a further embodiment. It is intended that the invention include these and other modifications and variations as coming within the scope and spirit of the invention.

FIGS. 1A and 1B are views of a conventional PEG tube device 10 having a base 12 and retainer balloon 13 made of conventional "soft" or elastomeric medical grade silicone in an un-stretched state (i.e., un-inflated condition) at the distal end of a catheter shaft 14. In FIG. 1B, the balloon 13 has been stretched by inflation to an inflated operational fill volume. As is well understood by those skilled in the art, the catheter shaft 14 is inserted into a stoma in a patient with the balloon 13 in an un-inflated state. Once the catheter shaft 14 is properly positioned in the stoma, a syringe (not shown) is inserted into a port 15 in the head 12 and a fluid is injected into the balloon 13 through an inflation valve within the head 12 and an inflation lumen configured in the catheter shaft 14 to inflate the balloon to an operational volume.

The balloons 13 of conventional PEG devices 10 illustrated in FIGS. 1A and 1B are made of elastomeric silicone and thus stretch or distend as they expand from the state depicted in FIG. 1A to their operational fill volume depicted in FIG. 1B, which requires a relatively large and continuous change in pressure to overcome the balloon's resistance to stretching. With these types of balloons 13, a leak in the balloon (or in the inflation lumen or inflation valve) may result in loss of substantially all of the inflation medium (e.g., saline or air) as the balloon 13 retracts to its un-inflated state (FIG. 1A). A PEG device 10 incorporating a conventional elastomeric balloon 13 will particularly benefit from an indicator in accordance with aspects of the present invention, as described in greater detail below.

Referring to FIGS. 2A and 2B, a balloon catheter device 18 incorporating aspects of the present invention is illustrated as an enteral feeding device 20. It should be appreciated that catheter devices 18 according to the invention are not limited to enteral feeding devices 20, and that the embodiments illustrated and described herein related to enteral feeding devices 20 are for illustrative purposes only. The enteral feeding device 20 is configured to provide a discrete visual indication or signal that the volume of fluid in the retention balloon has changed and that the balloon is no longer at its operational fill volume, which may be the result of a leak in the balloon.

The enteral feeding catheter device 20 includes a catheter 26 having a proximal end 28, a distal end 30, and catheter walls 32 defining a catheter lumen 34. A base 36 is located at the proximal end 28 of the catheter 26. The base 36 defines an opening 40 to the catheter lumen 34 and has a first end 42 and a second end 44. The assembly 10 includes an inflatable balloon 24 located at a distal end of the catheter.

The device 20 includes an inflation valve 46 located in the base 36 at the first end 42. The inflation valve 46 is in fluid communication with the balloon 24. This may be accomplished, for example, through an inflation lumen 52 (FIG. 3) defined by a portion of the wall 32 of the catheter 26 that extends between a cavity 50 (described in greater detail below) and the balloon 24, with the cavity 50 being in fluid communication with the inflation valve 46. An external inflation lumen or other configurations are also contemplated. The inflation valve may desirably be located in the first end 42 of the base.

The enteral feeding device 20 includes an indicator, generally 49, configured wholly or partially within the base 36. The indicator 49 does not utilize movable parts or components within the base 36 or attached to the base 36. Thus, the indicator 49 does not add to the overall dimensions of the base 36, particularly to the height or profile of the base 36 relative to a patient's skin, which is particularly desirable to patients. The indicator 49 is not prone to failure of movable mechanical parts, and does not significantly increase the complexity of the device 20. In a particular embodiment, the indicator 49 includes one or more internal cavities 50 defined at any desired location within the base 36. In FIGS. 2A and 2B, the internal cavity 50 is defined within the second end 44 of the base 36 generally opposite from the inflation valve 46 within the first end 42.

A translucent window 54 is disposed over the internal cavity 50 such that the internal volume of the cavity 50 is externally viewable through the base 36, more particularly through the window 54. This window 54 may be variously configured. For example, in the embodiment of FIGS. 2A, 2B, and 3, the translucent window 54 is defined by a translucent cap 60 that is fitted over an opening 55 in the base 36. The opening 55 may define all or a portion of the cavity 50. For example, the cap 60 may have a contour or radius so as to also define a portion of the cavity 50, as particularly seen in FIG. 3. Alternatively, the cap 60 may be a translucent plate-like member that is bonded to the base 36 over the opening 55. The cap 60 or other member forming the translucent window 54 is formed from any suitable translucent medical grade material. The translucent window 54 need not be clear, but is sufficiently translucent such that a patient or medical staff personnel can readily and visually discern the presence of inflation fluid within the internal cavity 50 through the window 54, as discussed in greater detail below.

The internal cavity 50 is in fluid communication with the balloon 24 by any suitable means. For example, in the embodiment of FIG. 3, a separate indicator lumen or passage 48 is defined in the base 36 between the inflation valve 46 and the cavity 50, with the cavity 50 being in fluid communication with the balloon 24 via the inflation lumen 52, as discussed above. Thus, the cavity 50 may be considered as "in series" between the inflation valve 46 and the balloon 24. With this configuration, without a vent passage defined in the flow path, air within the lumens 48, 52 and cavity 50 will be forced into the balloon 24 and simply act as a pressurizing medium and not adversely affect the indicator function of the cavity 50.

In other embodiments, one or more separate flow passages may be defined in the base 36 between the inflation valve 46 and the internal cavity 50. For example, FIG. 5B depicts a flow passage 56 disposed directly downstream of the inflation valve 46, around the circumference of the base 36, to the internal cavity 50, as well as a separate inflation lumen 52 between the inflation valve 46 and balloon 24.

Although not illustrated, it should be appreciated that the invention also encompasses a vent configuration, for example within the base 36, that vents any trapped air within the lumens 48, 52, 56 and cavity 50 so that the entire system is pressurized with inflation fluid injected through the inflation valve 46.

Because the internal cavity 50 is in fluid communication with the balloon 24, introduction of a colored (i.e., non-clear) fluid through the inflation valve 46 to inflate the balloon 24 results in the colored fluid 68 (FIG. 2B) flowing into the internal cavity 50 and being externally distinguishable through the translucent window 54, thereby providing an external visual indication of the inflation state of the balloon 24. Visual absence of the fluid 68 within the cavity 50 after placement of the device 20 in a patient and initial inflation of the balloon 24 to its operational fill volume is an indication that fluid has leaked from the balloon 24 or other component of the device 20, and that the balloon may not be sufficiently inflated to retain the catheter 26 in the patient's stoma.

As mentioned above, an additional or supplemental indicator may be provided within the internal cavity 50, for example a brightly colored ring, or patterned member 51 as indicated in the embodiment of FIG. 4B. The colored fluid would tend to obscure or alter the checkerboard pattern of the member 51, which provides an additional visually distinguishing indication of the inflation state of the balloon 24. For example, visual absence or change of visual state of the supplemental indicator 51 because of the presence of the colored fluid within the cavity 50 is also an indication that the balloon is inflated.

In the embodiment of FIG. 2B, the internal cavity 50 and associated translucent window 54 are defined at a single discrete location on the base 36, for example at a second end 44. FIG. 4A depicts an embodiment of a device 20 wherein multiple cavities 50 and associated translucent windows 54 are defined in the base 36 at different discrete locations on the base 36. FIG. 4B depicts an embodiment wherein the cavity 50 and translucent window 54 is defined as a continuous flow passage around the circumference of the base 36. These embodiments may be desired for providing the visual indicator 49 around a substantial portion of the base 36 such that a "reading" of the indicator 49 may be taken at various locations.

The translucent window 54 may be an insert 58 of translucent material that is fitted or bonded to the base 36 over the cavity 50, as depicted in FIGS. 4A and 4B. In an alternate embodiment, the portion of the base 36 in which the internal cavity 50 is formed (or the entire base 36) may be formed of an inherently translucent material such that the translucent window 54 is defined by the portion of the base 36 overlying the internal cavity 50, as depicted in FIGS. 5A and 5B.

As mentioned, the balloon of the invention may be a conventional elastomeric balloon, such as the balloon 13 described above with reference to FIGS. 1A and 1B. With this type of balloon 13, so long as the balloon is pressurized, fluid 68 will fill the internal cavity 50 and give an externally distinguishable visual indication that the balloon is inflated to at least some degree. If a leak develops in the balloon 13, the balloon will eventually contract to the state depicted in FIG. 1A, at which point the inflation fluid will also have drained from the internal cavity 50, thereby generating a visual indication of failure of the balloon 50.

The balloon 24 depicted in FIGS. 2A and 2B is distinguishable from the balloon 13 in FIGS. 1A and 1B. The balloon 24 has an initial collapsed and folded ("non-distended) state depicted by the phantom line 66. During inflation, the balloon 24 expands to the point in which the material that forms the balloon 24 is smooth and unfolded to an initial distended state, as depicted by the phantom line 62 in FIG. 2A. Essentially no pressure is required to fill the balloon 24 to this state other than to drive the liquid through the inflation lumen and unfold the balloon 24 because the material forming the balloon is not stretched to reach the initial distended state. The balloon is then pressurized and further distended to its operational fill volume. This fill volume of the balloon 24 is a volume in a range having a lower limit at the volume in which the material that forms the balloon first becomes smooth, unfolded and under a slight pressure but prior to any stretching of the material (state 62 in FIG. 2A), and an upper limit that is no more than 50% greater in volume than the lower limit (state 64 in FIG. 2A). In other words, the predetermined operation fill volume is a volume in a range with a lower limit at the balloon's transition from a non-distended state to an initial distended state at negligible pressure, and a upper limit that is no more than about 1.5 times (i.e., about fifty percent (50%) greater than) the volume of the balloon at the initial distended state. The volume at the lower limit of this range where the pressure of the fluid in the balloon is essentially zero is the "reserve volume". The pressure of fluid in the balloon increases when the balloon is filled past the reserve volume in a substantially linear relationship with additional increases in the volume of the balloon.

Various materials may used to form the inflatable balloon 24 in the embodiment of FIG. 2A. These materials include, but are not limited to, polyurethane (PU), low-density polyethylene (LDPE), polyvinyl chloride (PVC), polyamide (PA), or polyethylene teraphthalate (PETP). Additionally, copolymer admixtures for modifying the characteristics of the material may be used, for example a low density polyethylene and ethylene-vinylacetate copolymer (LDPE-EVA), or blends of the above mentioned materials (e.g. PU with PVC or PU with PA) would be considered suitable for forming the inflatable balloon having a predetermined fill volume. Other materials would also be suitable so long as they exhibit properties enabling them to be processed into an inflatable retention balloon having thin walls on the order of about 5 to about 100 micrometers as measured in the central region of the balloon. This thickness may be determined by conventional techniques utilizing a digital contact device such as, for example a Mitutoyo Litematic Digimatic Measuring Unit in accordance with the appropriate standardized tests. Desirably, the balloons may have thin walls in a range of between about 5 to about 50 micrometers, even more desirably, between about 5 to about 25 micrometers. Suitable materials should possess properties enabling them to be processed into an inflatable retention balloon having micro thin walls. In contrast, conventional silicone balloons have wall thicknesses of about 250 micrometers or even greater.

An advantage of utilizing such balloons 24 having a predetermined operational fill volume as described above is that if there is a leak or breach in the balloon or in another part of the system allowing fluid to escape, the balloon will depressurize to its initial distended state 62 wherein the balloon is at essentially zero pressure yet maintains the reserve volume of fluid, as discussed above. The reserve volume is less than the predetermined operational fill volume and reflects a volume of liquid that is retained in the balloon at about the transition from its non-distended state to its distended state. At the reserve volume, fluid may still be present in the internal cavity 50. However, exertion on the balloon by the patient will eventually cause loss of the reserve volume, more particularly loss of the fluid from the cavity 50.

While the present invention has been described in connection with certain preferred embodiments it is to be understood that the subject matter encompassed by way of the present invention is not to be limited to those specific embodiments. On the contrary, it is intended for the subject matter of the invention to include all alternatives, modifications and equivalents as can be included within the spirit and scope of the following claims.

What is claimed is:

1. An enteral feeding catheter assembly comprising:
   a catheter having a proximal end, a distal end, and catheter walls defining a catheter lumen;
   a base located at the proximal end of the catheter, the base defining an opening to the catheter lumen, the base having a first end and a second end;
   an inflatable balloon located at a distal end of the catheter,
   an inflation valve located on the base, the inflation valve in fluid communication with the balloon through an inflation lumen defined by the catheter walls;
   an internal cavity defined in the base, the cavity in fluid communication with the inflatable balloon such that fluid used to inflate the balloon to an operational fill volume fills the internal cavity as well; and
   a translucent window over the internal cavity such that an interior volume of the internal cavity is externally viewable;
   wherein introduction of a colored fluid to pressurize the balloon results in the colored fluid in the internal cavity, thereby providing an externally visual indication of the inflation state of the balloon.

2. The enteral feeding catheter assembly as in claim 1, where in the inflation valve is location on the first end of the base and the internal cavity and translucent window are located on the second end of the base.

3. The enteral feeding catheter assembly as in claim 1, wherein the internal cavity is in fluid communication in series between the inflation lumen and the balloon.

4. The enteral feeding catheter assembly as in claim 3, wherein the catheter defines a fluid flow passage between the inflation valve and the internal cavity, and an inflation lumen between the internal cavity and the balloon.

5. The enteral feeding catheter assembly of claim 1, wherein the inflatable balloon is an elastomeric balloon that essentially continuously stretches under increasing pressure from an un-inflated state to the operational fill volume.

6. The enteral feeding catheter assembly of claim 1, wherein the inflatable balloon is configured so as to unfold and expand from a non-distended state to an initial distended state with negligible inflation pressure, and to expand from the initial distended state to a predetermined operational fill volume at a substantially linear pressure increase, the balloon having a reserve volume of inflation fluid at the initial distended state.

7. The enteral feeding catheter assembly of claim 1, wherein the internal cavity and associated translucent window are defined at a single discrete location on the base or at a plurality of discrete locations on the base.

8. The enteral feeding catheter assembly of claim 1, wherein the translucent window comprises an insert disposed within the base.

9. The enteral feeding catheter assembly of claim 1, wherein a portion of the base in which the internal cavity is formed is translucent, the translucent window thereby defined by the portion of the base overlying the internal cavity.

10. The enteral feeding catheter assembly of claim 1, further comprising a source of fluid to inflate the balloon, the fluid having a color that is visually distinguishable through the translucent window.

* * * * *